United States Patent
Grigoriev et al.

(10) Patent No.: US 7,744,511 B2
(45) Date of Patent: Jun. 29, 2010

(54) SUIT FOR FORCEDLY MODIFYING A HUMAN POSTURE AND PRODUCING AN INCREASED LOAD ON A LOCOMOTION APPARATUS

(75) Inventors: Anatoly Ivanovich Grigoriev, Moscow (RU); Inesa Benediktovna Kozlovskaya, Moscow (RU); Evgeniy Petrovich Tihomirov, Moscow (RU); Elena Illarionovna Sorokina, Moskovskaya obl. (RU)

(73) Assignee: State Scientific Center of Russian Federation - Institute of Bio-Medical Problems of the Russian Academy of Sciences, Moscow (RU)

( * ) Notice: Subject to any disclaimer, the term of this patent is extended or adjusted under 35 U.S.C. 154(b) by 10 days.

(21) Appl. No.: 10/598,244
(22) PCT Filed: Feb. 26, 2004
(86) PCT No.: PCT/RU2004/000069
§ 371 (c)(1), (2), (4) Date: Aug. 22, 2006
(87) PCT Pub. No.: WO2005/082295
PCT Pub. Date: Sep. 9, 2005

(65) Prior Publication Data
US 2007/0135278 A1 Jun. 14, 2007

(51) Int. Cl.
*A63B 21/02* (2006.01)
(52) U.S. Cl. .......................... 482/124; 482/43; 482/121
(58) Field of Classification Search ................. 482/121, 482/124, 43
See application file for complete search history.

(56) References Cited

U.S. PATENT DOCUMENTS

| | | | | |
|---|---|---|---|---|
| 807,908 A | * | 12/1905 | Bradstreet | 482/51 |
| 2,097,376 A | * | 10/1937 | Marshman | 482/124 |
| 3,162,442 A | * | 12/1964 | Laddie | 482/124 |
| 3,295,517 A | * | 1/1967 | Stevens | 602/19 |

(Continued)

FOREIGN PATENT DOCUMENTS

RU 2040923 9/1995

(Continued)

*Primary Examiner*—Steve R Crow
*Assistant Examiner*—Robert F Long
(74) *Attorney, Agent, or Firm*—Brooks Kushman P.C.

(57) ABSTRACT

The invention relates to medicine and is used for forcedly modifying a human posture and producing an increased load on a locomotion apparatus. The inventive device comprises shoulder, pelvic, knee and foot supports which are connected to each other by loading elements each of which is embodied in the form of an inextansible strip and an avoid of residual deformation elastic rod fixed thereto. Said device also comprises a support arranged on the thoracic surface of the body which is connected to the shoulder supports with the aid of self-fixing buckles, thereby forming a vest which tightly embraces a patient body. The pelvic support is embodied in the form of shorts. Said thoracic and pelvic supports are provided with load strips which are sewed therein and provided with buckles for fixing said thoracic and pelvic supports to each other. The knee supports are embodied in the form of a binder in such a way that it tightly embraces a knee-joint area, the upper quarter of a leg and the lower quarter of a hip.

10 Claims, 5 Drawing Sheets

U.S. PATENT DOCUMENTS

Figure 1:
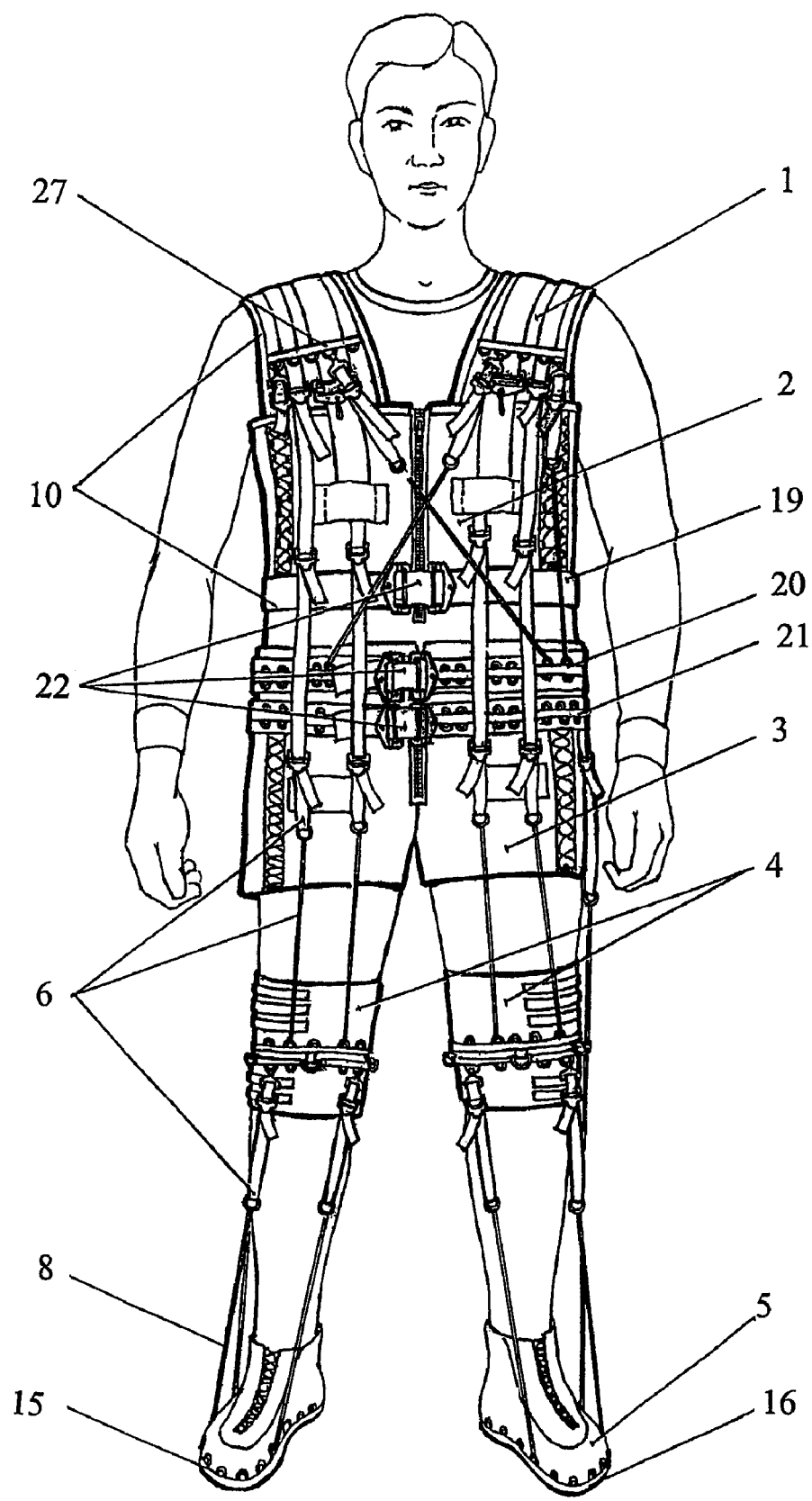

| Patent No. | | Date | Inventor | Class |
|---|---|---|---|---|
| 3,613,679 | A * | 10/1971 | Bijou | 602/75 |
| 4,658,442 | A * | 4/1987 | Tomlinson et al. | 2/94 |
| RE32,547 | E * | 11/1987 | Reed et al. | 119/702 |
| 5,129,647 | A * | 7/1992 | Castellanos | 482/124 |
| 5,144,694 | A | 9/1992 | Conrad da oud et al. | |
| 5,308,305 | A * | 5/1994 | Romney | 482/124 |
| 5,372,565 | A * | 12/1994 | Burdenko | 482/124 |
| 5,647,827 | A * | 7/1997 | Gutkowski et al. | 482/124 |
| 5,683,336 | A * | 11/1997 | Pape | 482/124 |
| 5,700,231 | A * | 12/1997 | Wilkinson | 482/124 |
| 5,716,307 | A * | 2/1998 | Vadher | 482/125 |
| 5,720,042 | A * | 2/1998 | Wilkinson | 2/69 |
| 5,779,659 | A * | 7/1998 | Allen | 602/75 |
| 5,784,716 | A | 7/1998 | Holt et al. | |
| 5,792,034 | A * | 8/1998 | Kozlovsky | 482/124 |
| 5,803,881 | A * | 9/1998 | Miller | 482/124 |
| 5,813,955 | A * | 9/1998 | Gutkowski et al. | 482/124 |
| 5,820,534 | A * | 10/1998 | Vadher | 482/124 |
| 5,857,945 | A * | 1/1999 | Papp et al. | 482/124 |
| 5,867,826 | A * | 2/1999 | Wilkinson | 2/69 |
| 5,875,491 | A * | 3/1999 | Wilkinson | 2/69 |
| 5,978,966 | A * | 11/1999 | Dicker et al. | 2/69 |
| 5,993,361 | A * | 11/1999 | Paoli et al. | 482/121 |
| 5,993,362 | A * | 11/1999 | Ghobadi | 482/124 |
| 6,007,463 | A * | 12/1999 | Wells et al. | 482/126 |
| 6,171,274 | B1 * | 1/2001 | Nafpliotis | 602/75 |
| 6,179,760 | B1 * | 1/2001 | Rumbaugh | 482/121 |
| 6,213,922 | B1 * | 4/2001 | Afanasenko et al. | 482/124 |
| 6,287,242 | B1 * | 9/2001 | Fray | 482/121 |
| D455,185 | S * | 4/2002 | Karadimas | D21/692 |
| 6,364,851 | B1 * | 4/2002 | Nafpliotis | 602/19 |
| 6,368,256 | B1 * | 4/2002 | Rumbaugh | 482/121 |
| D457,965 | S * | 5/2002 | Firer | D24/190 |
| 6,656,097 | B2 * | 12/2003 | Karecki | 482/148 |
| 6,659,921 | B2 * | 12/2003 | Vernon | 482/124 |
| 6,691,318 | B1 * | 2/2004 | Davis | 2/102 |
| 6,709,369 | B1 * | 3/2004 | Jacobs | 482/80 |
| 7,041,074 | B1 * | 5/2006 | Averianov et al. | 602/20 |
| 7,153,246 | B2 * | 12/2006 | Koscielny et al. | 482/121 |
| 7,553,266 | B2 * | 6/2009 | Abdoli-Eramaki | 482/124 |
| 2001/0007845 | A1 * | 7/2001 | Afanasenko et al. | 482/124 |
| 2001/0029224 | A1 * | 10/2001 | Karecki | 482/148 |
| 2002/0187884 | A1 * | 12/2002 | McGrath | 482/121 |
| 2003/0027698 | A1 * | 2/2003 | Matsuoka | 482/124 |
| 2003/0045408 | A1 * | 3/2003 | Seles | 482/121 |
| 2003/0092545 | A1 * | 5/2003 | Koscielny et al. | 482/124 |
| 2003/0120183 | A1 * | 6/2003 | Simmons | 600/595 |
| 2006/0033713 | A1 * | 2/2006 | Pryor | 345/158 |
| 2007/0004570 | A1 * | 1/2007 | Afanasenko et al. | 482/124 |
| 2007/0083975 | A1 * | 4/2007 | Senegal | 2/102 |
| 2007/0135279 | A1 * | 6/2007 | Purdy et al. | 482/124 |
| 2007/0213186 | A1 * | 9/2007 | Longo | 482/121 |

FOREIGN PATENT DOCUMENTS

| | | |
|---|---|---|
| RU | 2131232 | 6/1999 |
| RU | 2201177 | 9/2002 |

* cited by examiner

SUIT FOR FORCEDLY MODIFYING A HUMAN POSTURE AND PRODUCING AN INCREASED LOAD ON A LOCOMOTION APPARATUS

This invention relates to medicine and, more specifically, to treatment of neurological, muscular and orthopedic diseases accompanied with disorders of the locomotor apparatus or central movement regulation system in children and adults. The device may be also used for training sportsmen or physical workout of long-time bed patients.

Its sangenetic mechanisms are based on the following factors:

(a) producing (or increasing) a longitudinal load on the skeleton's structures;

(b) increasing the muscular load during movements;

(c) activation of the supporting reception.

These features of the body suit enable it to counteract the pathological postural orientation typical of many disease states (e.g., infantile cerebral palsy, stroke, etc.). This results in a tendency for normalizing the mechanisms of regulation of the vertical posture and loco motions.

Known in the art there is a body suit for medico-conductive rehabilitation of neurological patients diagnosed with locomotory impairment, described in the RU Patent No. 2201177 (2000, V. A. Isanov), which includes a union suit filled with oxygen under pressure. The disadvantage of this device resides in its complexity and the need for gas containers.

There are other designs of prior art devices used for rehabilitation of the said groups of patients. These are described in:

1. The RF patent No. 2040923 (1995). V. P. Tychina. METHOD AND ORTHOPEDIC DEVICE FOR TREATING SPASTIC FORMS OF CEREBRAL INFANTILE PARALYSIS 2. The RF patent No. 2054907 (1996). N. I. Afanasenko et al. DEVICE FOR TREATING PATIENTS WITH DISTORTED POSTURE AND DISTURBED MOTOR ACTIVITY;

3. The RF patent No. 2131232 (1999). A. I. Averianov et al. UNION SUIT FOR TREATMENT OF PATIENTS WITH INFANTILE CEREBRAL PARALYSIS AND PATIENTS WITH AFTEREFFECTS OF CRANIOCEREBRAL INJURY (prototype).

All the designs cited above, including the prototype one, have a number of common disadvantages decreasing the effectiveness of the clinical effect of such designs and, more specifically, the load-bearing elements of the devices performed as elements of type shoulder pads, belts for lumbar, knee, ankle joint and shoulders, and bandages, though they have their distinctive features. The area of contact with the human body in such devices is too small and their locking is not good enough. Sometimes this leads to impossibility of asymmetrically loading the skeletal muscles, which is one of the principal factors in correcting the positions of the body parts relatively one another. For example, the shoulder pads having a small contact area with inadequate means for transmission of the load to them cannot stay motionless when the different pull forces are made from the breast and back loading elements, while their movement equalizes the pull forces vectored fore and aft, thus nullifying the intention to change the orientation of the body towards bending.

Besides, to the disadvantages of the known devices, including the prototype one, should be referred the fact that the elastic ties are not calibrated, they were fabricated from materials having no constant "stretch-force" characteristic. The number of attachment points for the elastic ties in such devices is insufficient.

The engineering problem to be solved by the claimed invention is providing a device capable of producing a stable asymmetrical selective load on the skeletal muscles by increasing the area of contact of the device with the patient's body, better interlocking of its components while preserving the flexibility of its joints and allowing for selective energetic loading of individual kinds of movements.

The loading elements of the claimed suit act directly on both the wearer's musculoskeletal system and the central representation of the motor analyzer.

The design of the device enables to load the musculoskeletal system or change the position of parts of the body relatively one another "in stages" by applying pressure to the following zones:

1. From foot to knee;
2. From waist to knee (from waist to foot);
3. From shoulders to waist (from shoulder to knee, from shoulders to foot).

A possibility of selectively act on one (right or left) half of the body seems to be of importance. A need for this may arise in treatment of diseases, which affect one half of the body (e.g., the stroke, hemiparetic form of infantile cerebral palsy). A significant role in the sangenetic mechanism of action of the device is irritation of the receptors distributed in the ligaments and joints, notably by a pressure on the foot planta, caused by tensioning of the loading elements attached to the foot pad, which is an adequate irritator of the Vater-Pacini receptor corpuscles initiating the reflex chain of automatic movement control.

The stimulation of this mechanism is particularly useful for long-time bed patients.

An example, the need for a forced change of a man's posture is the infantile cerebral palsy patient with symptoms characterized by a change in the position of the body parts respectively one another (a hanging foot, triple bend syndrome, etc.).

The triple bend syndrome is the most illustrative case because the essence of the treatment is the struggle against the bending orientation in the knee and hip joints and in the spinal chord.

To allow for application of a partial pressure to the locomotor apparatus, the hinges attaching the loading elements are arranged in four stages:

Stage 1—breast and back hinges, near the shoulder girdles;
Stage 2—lumbar area, hinges are attached by belts on the entire perimeter;
Stage 3—knee joint, front and side surfaces;
Stage 4—foot, hinges are arranged on the welt or the foot loop embracing the shoe.

The claimed objective is achieved by the known device used for forced change of man's posture and producing an increased load on the locomotor apparatus, comprising the shoulder, pelvic, knee and foot pads all interconnected by loading elements, wherein each loading element is an inextensible adjusting band and elastic tie without residual deformation attached to it and having an initial length, which, if it is increased, creates a force of at least 4 kg; and the ratio between the lengths of the adjusting bands and elastic ties of each loading element being selected such that the maximum elongation of the elastic tie is at least 50% the initial length; the device additionally comprises a pad, which is arranged on the thoracic part of the trunk and connected with the shoulder pads with use of self-locking buckles, thus forming a vest tightly fitting on the patient's body, the pelvis pad is designed as shorts, both the breast and pelvis pads are having sewed-in load-bearing bands with buckles for interlocking of the breast and pelvis pads, the pads are designed so that they can be individually fitted on the patient's body using of additional attachments, the knee joint pads are bandages that can tightly fit around the knee joint, upper quarter of the shin-bone and lower quarter of the hip, and there are hinges arranged on bandage in the plane (along the axis) of the knee joint to accommodate the loading ties, the foot pads are made in the form shoes provided on the foot perimeter with a fabric strip carrying hinges to attach to them the elastic ties, the step between the hinges being not over 10% of the shoe sole length, or the foot pads are flexible fabric plates capable of embracing them the entire sole of the patient and carrying hinges to attach to them the ties producing the load, the device is additionally provided with three belts, each having two self-tightening locks designed to enable locating the first belt of these belts along the edges of the costal arch, the second belt on the waist and the third belt on the patient's hucklebones, each belt also having a fabric fastener on the interior surface of that part of the belt, which is arranged on the patient's body back surface; the breast and pelvis pads have the mating parts of the fastener; the adjusting bands of the loading elements are rigidly attached to the front, side and rear surfaces of the breast and pelvis pads but their ends performed free and provided with buckles and hooks.

The additional attachments enabling coarse individual fitting of the breast and pelvis pads around the patient may be designed as pleats performed on the side of the pads corresponding to the back and side surfaces of the trunk and fitted n zip fasteners (n being not less than 2), which provide, when locked, obtaining n+1 standard sizes.

The additional attachments enabling fine individual fitting of the breast and pelvis pads of the device on the patient may be designed as a lacing arranged on the front and back surfaces of the pads.

The tight fitting of the pad around the limb near the knee joint may be achieved by using stretch-proof adjusting bands that are rigidly attached to the entire front surface and whose free ends are provided with self-locking fabric fasteners.

Each loading element may be provided with a dynamometric tape to check the pulling force.

All the pads may carry hinges to attach the tensioning elements. On all the belts, the hinges for attachment of the tensioning elements may be arranged on two loop bands one of these may have the hinges facing up and the other of these—down.

A coordinate net may be applied to the surfaces of all the pads, making it possible to register the locking points and direction of the pulling force.

Figure 2:
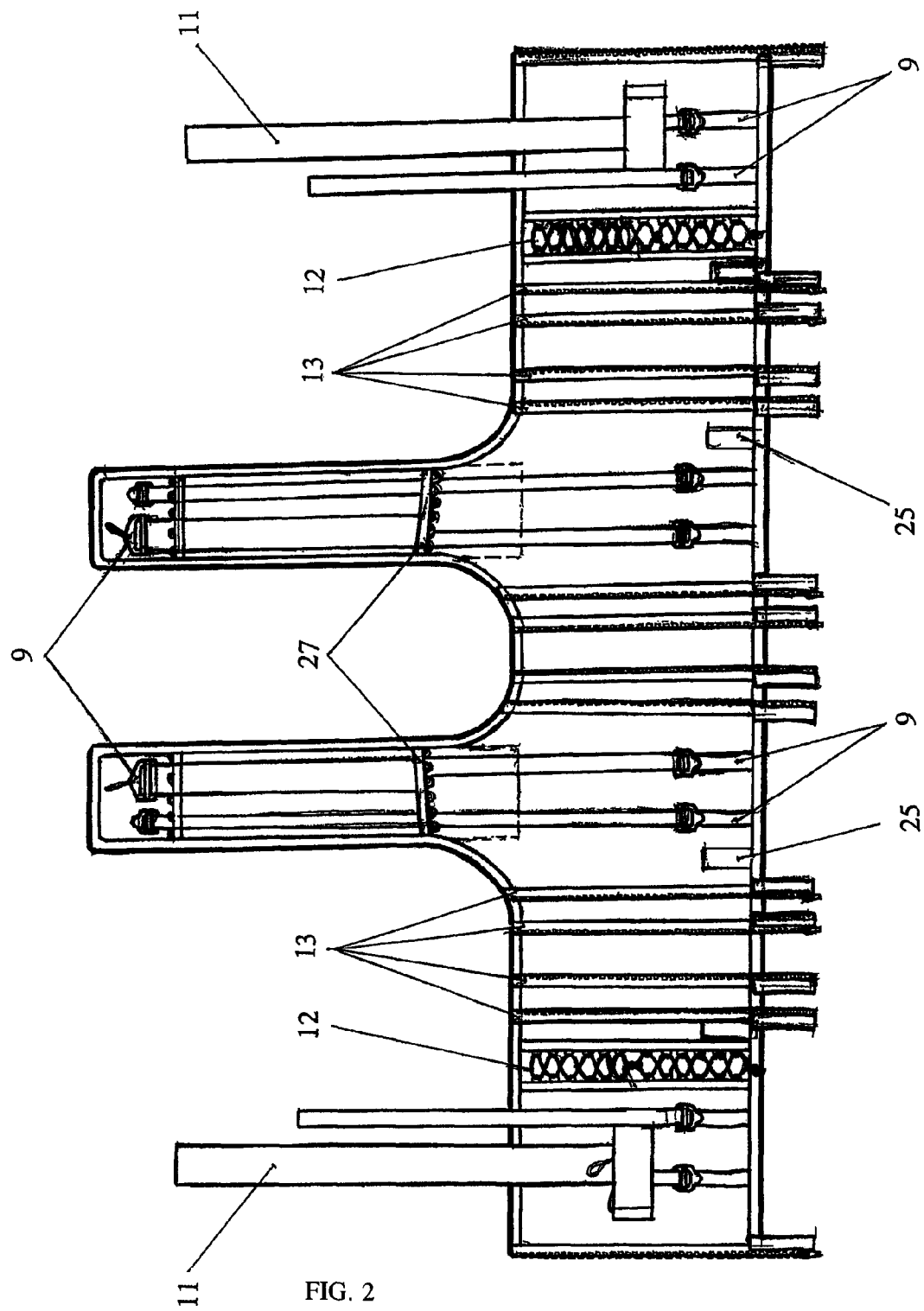
Figure 3:
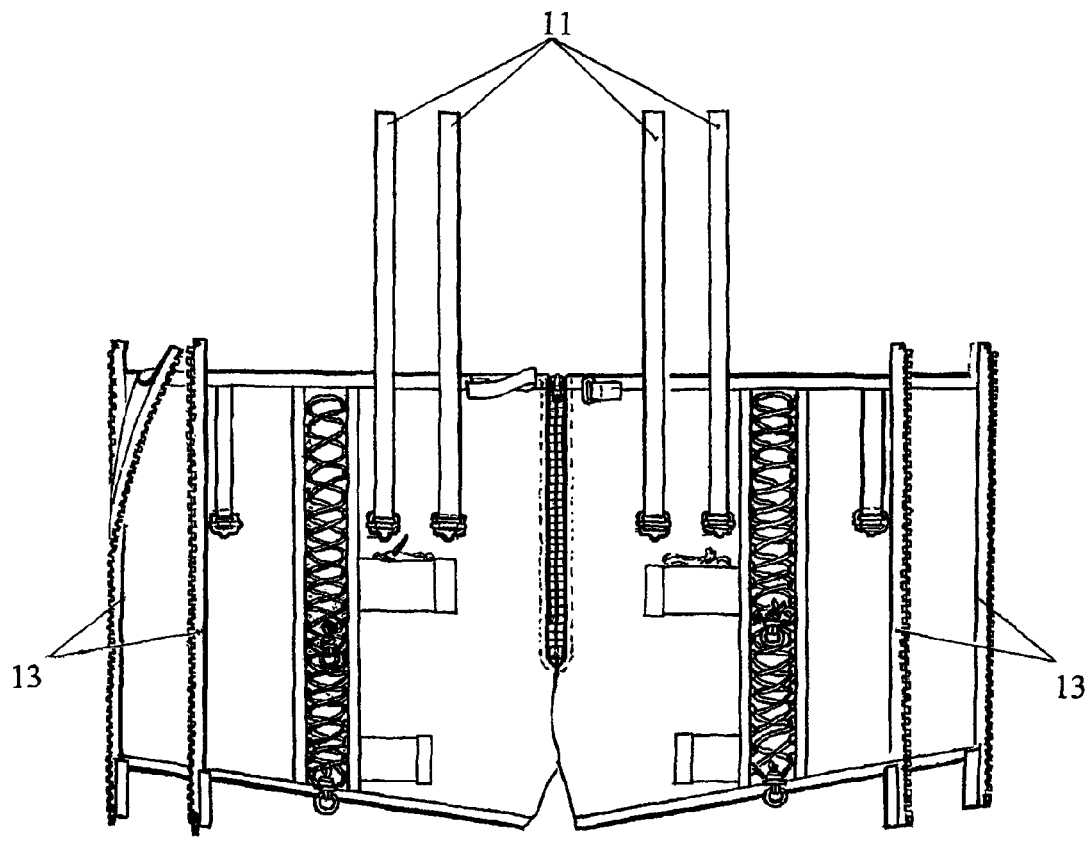
Figure 4:
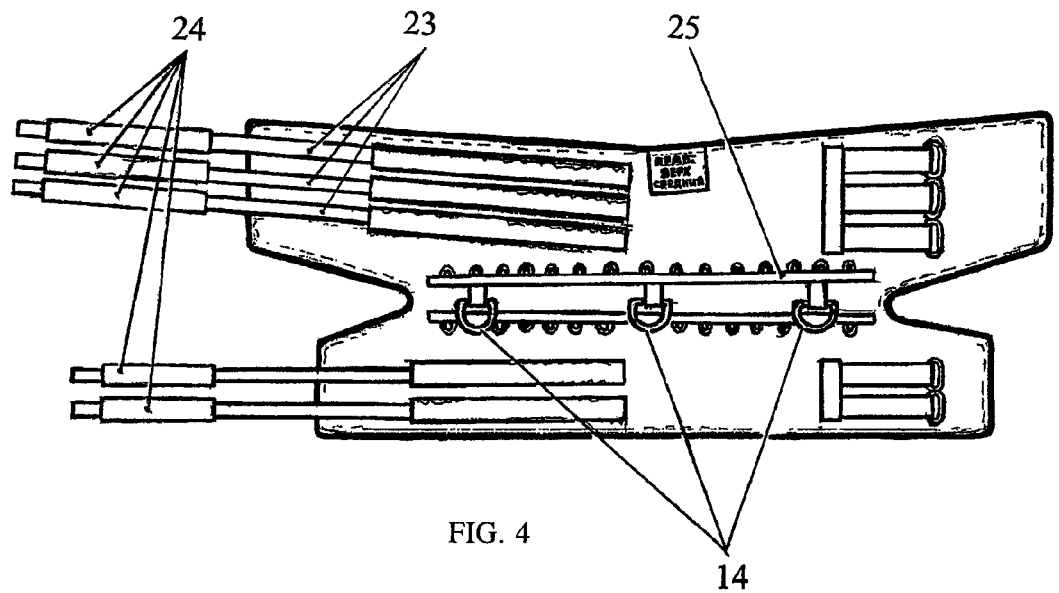
Figure 5:
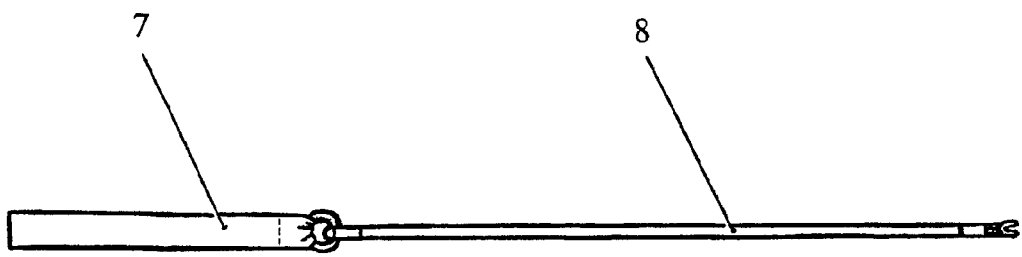
Figure 6:
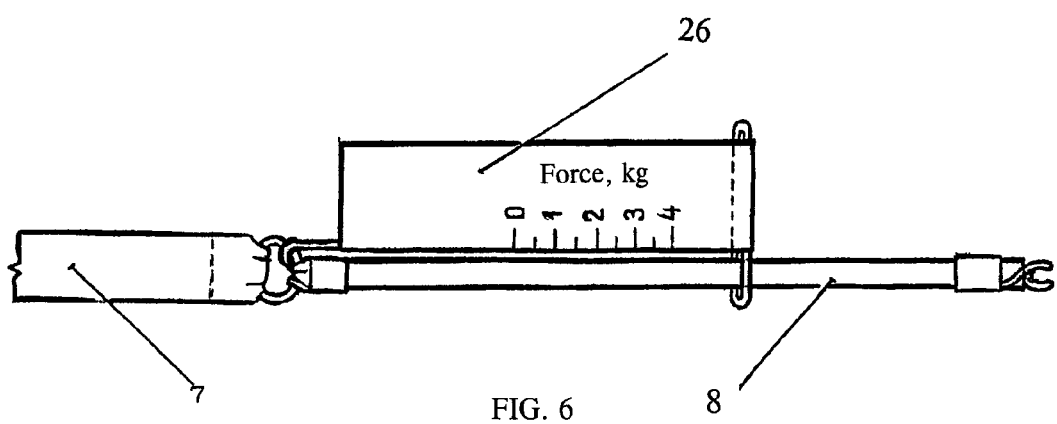
Figure 7:
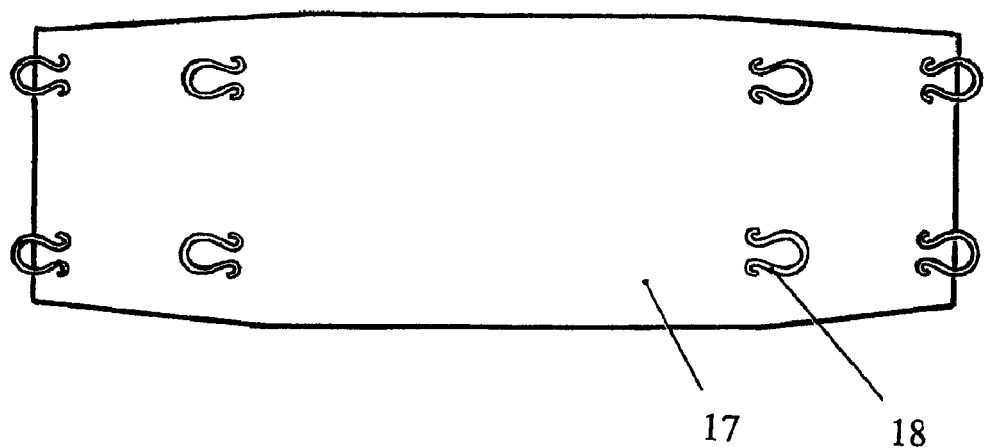
Figure 8:
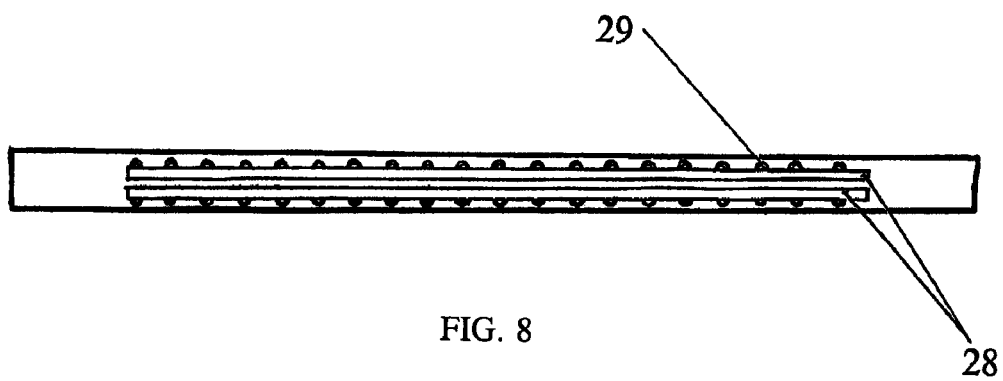
Figure 9:
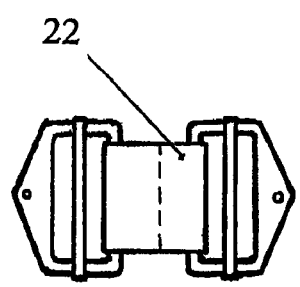

The essence of the claimed device may be clear from the following illustrations:

FIG. 1—Front view of device;
FIG. 2—Vest;
FIG. 3—Shorts;
FIG. 4—Knee pad;
FIG. 5—Loading element;
FIG. 6—Dynamometric tape;
FIG. 7—Foot pad;
FIG. 8—Belt;
FIG. 9—Double buckle for belt.

The device comprises a shoulder pad (1), breast pad (2), pelvis pad designed as shorts (3), knee pads (4) performed as bandages and foot pads (5), all connected together by means of the loading elements (6) with a possibility of being disconnected; each loading element (6) is an extensible adjusting band (7) and an elastic tie (8) attached to it; the breast pad (2) arranged on the thoracic part of the trunk and connected with the pads on the shoulder girdles (1) by self-locked buckles (9) thus forming a vest (10) tightly fitting around the patient's body, both the breast (2) and pelvis pads (3) have sewed-in load-bearing bands (11) with buckles (9) for interlocking the breast and pelvis pads, these pads are designed to enable their coarse and fine fitting on the patient's body with the aid of additional attachments (12, 13); the knee pad bandage area arranged along the joint's horizontal axis is provided with hinges (14) to carry the ties (8) of the loading elements (6); the foot pads (5) are designed either as shoes with the fabric strip (15) provided on the sole perimeter and carrying hinges (16) to attach the elastic ties (8) or the foot pads (5) are flexible fabric plates (17) performed so as to be able to embrace the entire sole of the patient and carrying hinges (18) to attach to them the elastic ties (8), the device has three belts (19, 20, 21), each of them have two self-tightening locks (22), one of the belts being designed so that it can be arranged along the edges of the costal arch (19) and the other belt (20)—on the waist, and the third belt (21)—on the patient's ileac bones, each belt also carrying a fabric fastener on its inside surface part, which is arranged on the patient's back surface; the breast (2) and pelvis (3) pads having mating parts of the fastener; the adjusting bands (7) of the loading elements (6) are rigidly attached to the front, side and rear surfaces of the breast (2) and pelvis (3) pads, but their ends is performed free and provided with buckles and hooks.

The additional attachments (12) enabling coarse individual fitting of the breast and pelvis pads around the patient are essentially pleats provided with zip fasteners.

The additional attachments (13) enabling fine individual fitting of the breast and pelvis pads on the patient may be performed as a lacing. The bandage applied to the knee joint area (4) may carry inextensible adjusting bands (23), which are arranged over the entire front surface, and whose free ends are provided with a self-locking fabric fastener (24). The knee joint pad (4) may have two rows of hinges (25) one of these has hinges facing up and the other of these—down.

Each loading element (6) may be provided with a dynamometric tape (26) to check the pulling force.

All the pads, (1) through (5), may carry hinges (27) to attach the loading elements (6).

All the belts, (19, 20, 21) may carry hinges arranged on two bands (28) and (29), one of these has hinges facing up and the other of these—down.

The claimed device shall be used as follows.

Knowing the dimensions of the patient's body and before putting the suit on, coarse-fit is performed of the breast (2) and pelvis (3) pads to the required size using the zip fasteners (additional attachment 13) forming pleats around the breast (2) and pelvic (3) pads, then the shoulder (1) and breast (2) pads are dressed, connecting the left and right sides by using the zip fastener (13), the breast and pelvis pads are linked up by load-bearing bands (11) using the buckles (9), and the suit are adjusting for the patient's height, following which, fine-fit of the suit is performing to the patient's body using the lacing (additional attachment 12), striving for tightly fitting the suit on the patient's body. Now the knee pads (4) are applied also making these fit tightly around the knees, and the shoes (15) with hinge bands (16) are put on following which the belts (19, 20. 21) are tighten using locks (22). Then the loading elements (6) are locked, which shall always be positioned with the adjusting bands (7) at the top and are distributed them over the front, back and side surfaces of the trunk and legs of the patient as prescribed by the doctor, and now preliminary slack symmetrical tension of them are performed (front-back, right-left), the indications of the dynamometric tapes (26) are added together and further (if the indications so dictate) selective of the loading elements (6) are performed in order to obtain the desired effect in changing the posture (changing the angles in the hip, knee, and ankle joints, position of the foot, decreasing the bending orientation etc.).

Now session of the physical exercises are proceeded, e.g. walking or a special program workout.

The invention claimed is:

1. A device for forced change of a user's posture and producing an increased load on the locomotor apparatus, the device comprising:
    a pair of shoulder pads, a pelvic pad, a pair of knee pads and a pair of foot pads all interconnected by a plurality of loading elements;
    a breast pad arranged on the thoracic part of the trunk and connected to the shoulder pads by use of self-locking buckles, forming a vest tightly fitting on the user's body, wherein each loading element is an inextensible adjusting band and elastic tie without residual deformation attached to the band, the tie having an initial length, which, if it is extended, creates a force of at least 4 kg, and where the ratio between the lengths of the adjusting band and elastic tie of each loading element being selected such that the maximum elongation of the elastic tie is at least 50% of the initial length;
    wherein both the breast and pelvis pads have sewed-in load-bearing bands with buckles for interlocking of the breast pad to the pelvis pad, the pads designed so that they can be individually fitted on the user's body using of additional attachments, the adjusting bands of the loading elements rigidly attached to the front, side and rear surfaces of the breast and pelvis pads and the ends of the adjusting bands are provided with buckles and hooks;
    wherein the device is additionally provided with three belts, each belt having two self-tightening locks designed to enable locating the first belt of these belts along the edges of the costal arch, the second belt on the waist and the third belt on the user's huckle-bones, each belt also having a fabric fastener on the interior surface of that part of the belt, which is arranged on the back surface of the user's body, the mating parts of the fastener located on the breast and pelvis pads;
    wherein the pair of knee pads are bandages that can tightly fit around a knee joint, an upper quarter of the shin-bone and a lower quarter of the hip, each knee pad having hinges arranged on the bandage in the plane of the knee joint to accommodate the adjusting band, and where the foot pads are in the form of shoes and a plurality of hinges extend from the shoes, the hinges being capable of attaching to the elastic ties, and the step between the hinges on one side of the shoe is less than 10% of the shoe sole length; and
    wherein additional attachments enabling fine individual fitting of the breast and pelvis pads of the device on the user are designed as a lacing arranged on the front and back surfaces of the pads wherein each loading element is provided with a dynamometric tape to check and provide feedback of the pulling force in order to adjust said loading elements to achieve the desired force for exercise therapy.

2. A device of claim 1, wherein additional attachments enabling coarse individual fitting of the breast and pelvis pads around the user are pleats made on the side of the pads corresponding to the back and side surfaces of the trunk and fitted with n zip fasteners (n being not less than 2), which provide, when locked, obtaining n+1 standard sizes of the pads.

3. A device of claim 1, wherein tight fitting of pad around the limb near the knee joint is provided using of stretch-proof adjusting bands, which are rigidly attached to the entire front surface and whose free ends are provided with self-locking fabric fasteners.

4. A device of claim 1, wherein all the pads carry hinges to attach the loading elements.

5. A device of claim 1, wherein the hinges for attachment of the tensioning elements are arranged on two loop bands wherein one of these has the hinges facing up and the other of these—down.

6. The device of claim 1 wherein the shoe is provided with a fabric strip on the perimeter, the fabric strip carrying the show hinges which attach to the elastic ties.

7. The device of claim 1 wherein the shoe is a flexible fabric plate capable of embracing the entire sole of the user, the fabric plate carrying the hinges which attach to the elastic ties.

8. A device for forced change of a user's posture and producing an increased load on the locomotor apparatus, the device comprising:
    a pair of shoulder pads, a pelvic pad, a pair of knee pads and a pair of foot pads all interconnected by a plurality of loading elements;
    a breast pad arranged on the thoracic part of the trunk and connected to the shoulder pads by use of self-locking buckles, forming a vest tightly fitting on the user's body, wherein each loading element is an inextensible adjusting band and elastic tie without residual deformation attached to the band, the tie having an initial length, which, if it is extended, creates a force of at least 4 kg, and where the ratio between the lengths of the adjusting band and elastic tie of each loading element being selected such that the maximum elongation of the elastic tie is at least 50% of the initial length;
    wherein both the breast and pelvis pads have sewed-in load-bearing bands with buckles for interlocking of the breast pad to the pelvis pad, the pads designed so that they can be individually fitted on the user's body using of additional attachments, the adjusting bands of the loading elements rigidly attached to the front, side and rear surfaces of the breast and pelvis pads and the ends of the adjusting bands are provided with buckles and hooks;
    wherein a coarse individual fitting of the breast and pelvis pads around the user can be made through a series of pleats made on the side of both of the pads corresponding to the back and side surfaces of the trunk of the user, the pleats fitted with n zip fasteners (n being not less than 2), which provide n+1 standard sizes of the breast and pelvis pad;
    wherein the device is additionally provided with three belts, each belt having two self-tightening locks designed to enable locating the first belt of these belts along the edges of the costal arch, the second belt on the waist and the third belt on the user's huckle-bones, each belt also having a fabric fastener on the interior surface of that part of the belt, which is arranged on the back surface of the user's body, the mating parts of the fastener located on the breast and pelvis pads;
    wherein the pair of knee pads are bandages that can tightly fit around a knee joint, an upper quarter of the shin-bone and a lower quarter of the hip, each knee pad having hinges arranged on the bandage in the plane of the knee joint to accommodate the adjusting band, and where the foot pads are in the form of shoes to accommodate the elastic ties; and wherein each loading element is provided with a dynamometric tape to check and provide feedback of the pulling force in order to adjust said loading elements to achieve the desired force for exercise therapy to check the pulling force.

9. The device of claim 8 wherein the shoes further comprise a plurality of hinges extending from each shoe, the hinges being capable of attaching to the elastic ties, and the step between the hinges on one side of the shoe is less than 10% of the shoe sole length.

10. The device of claim 8, wherein additional attachments enabling fine individual fitting of the breast and pelvis pads of the device on the user are designed as a lacing arranged on the front and back surfaces of the pads.

* * * * *